US007376468B2

(12) United States Patent
King et al.

(10) Patent No.: US 7,376,468 B2
(45) Date of Patent: *May 20, 2008

(54) APPARATUS AND METHOD FOR EXPANDING A STIMULATION LEAD BODY IN SITU

(75) Inventors: Gary W. King, Fridley, MN (US); Mark T. Rise, Monticello, MN (US); Michael J. Schendel, Andover, MN (US); Richard Schallhorn, Lake Elmo, MN (US)

(73) Assignee: Medtronic, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 10/767,244

(22) Filed: Jan. 27, 2004

(65) Prior Publication Data

US 2004/0186543 A1 Sep. 23, 2004

Related U.S. Application Data

(60) Continuation of application No. 10/158,521, filed on May 30, 2002, now Pat. No. 6,714,822, which is a division of application No. 09/862,104, filed on May 21, 2001, now Pat. No. 6,442,435, which is a continuation of application No. 09/584,572, filed on May 31, 2000, now Pat. No. 6,292,702, which is a division of application No. 09/070,136, filed on Apr. 30, 1998, now Pat. No. 6,161,047.

(51) Int. Cl.
*A61N 1/05* (2006.01)
(52) U.S. Cl. .................................................. 607/116
(58) Field of Classification Search ........ 607/116–119, 607/122–128, 62
See application file for complete search history.

(56) References Cited

U.S. PATENT DOCUMENTS 4,141,365 A 2/1979 Fischell et al.

(Continued)

FOREIGN PATENT DOCUMENTS

EP 0104287 4/1984

(Continued)

OTHER PUBLICATIONS

Analysis of Current Density and Related Parameters In Spinal Cord Stimulation, Wesselink et al., IEEE, Transactions of Rehabilitation Engineering, vol. 6, pp. 200-207, 1998.

(Continued)

*Primary Examiner*—George R. Evanisko
(74) *Attorney, Agent, or Firm*—Rick L. Franzen

(57) ABSTRACT

An implantable lead is provided with at least one extendable member to position therapy delivery elements, which may be electrodes or drug delivery ports, after the lead has been inserted into the body. The lead may formed as a resilient element which is contained in a retainer tube that may be removed to permit the lead to deploy. Alternatively, a non-resilient lead may be provided with a slotted retainer tube. A series of mechanical linkages for expanding and retracting the lead within the human body may be actuated with various mechanisms. A control system may be provided for closed-loop feedback control of the position of the extendable members. The invention also includes a method for expanding an implantable lead in situ.

12 Claims, 15 Drawing Sheets

U.S. PATENT DOCUMENTS

| | | |
|---|---|---|
| 4,154,247 A | 5/1979 | O'Neill |
| 4,166,469 A | 9/1979 | Littleford |
| 4,285,347 A | 8/1981 | Hess |
| 4,304,239 A | 12/1981 | Perlin |
| 4,351,330 A | 9/1982 | Scarberry |
| 4,374,527 A | 2/1983 | Iversen |
| 4,379,462 A | 4/1983 | Borkan et al. |
| 4,414,986 A | 11/1983 | Dickhudt et al. |
| 4,419,819 A | 12/1983 | Dickhudt et al. |
| 4,519,403 A | 5/1985 | Dickhudt |
| 4,522,212 A | 6/1985 | Gelinas et al. |
| 4,549,556 A | 10/1985 | Tarjan et al. |
| 4,590,949 A | 5/1986 | Pohndorf |
| 4,640,298 A | 2/1987 | Pless et al. |
| 4,658,835 A | 4/1987 | Pohndorf |
| 4,692,147 A | 9/1987 | Duggan |
| 4,699,147 A | 10/1987 | Chilson et al. |
| 4,800,898 A | 1/1989 | Hess et al. |
| 4,989,617 A | 2/1991 | Memberg et al. |
| 5,010,894 A | 4/1991 | Edhag |
| 5,056,532 A | 10/1991 | Hull et al. |
| 5,113,859 A | 5/1992 | Funke |
| 5,117,828 A | 6/1992 | Metzger et al. |
| 5,121,754 A | 6/1992 | Mullett |
| 5,143,067 A | 9/1992 | Rise et al. |
| 5,215,103 A | 6/1993 | Desai |
| 5,255,678 A | 10/1993 | Deslauriers |
| 5,259,387 A | 11/1993 | de Pinto |
| 5,282,468 A | 2/1994 | Klepinski |
| 5,344,439 A | 9/1994 | Otten |
| 5,365,926 A | 11/1994 | Desai |
| 5,370,679 A | 12/1994 | Atlee, III |
| 5,391,200 A | 2/1995 | KenKnight et al. |
| 5,397,339 A | 3/1995 | Desai |
| 5,397,342 A | 3/1995 | Heil, Jr. et al. |
| 5,407,453 A | 4/1995 | Pierce-Ruhland et al. |
| 5,409,453 A | 4/1995 | Lundquist et al. |
| 5,417,719 A | 5/1995 | Hull et al. |
| 5,423,864 A | 6/1995 | Ljungstroem |
| 5,431,696 A | 7/1995 | Atlee, III |
| 5,458,629 A | 10/1995 | Baudino et al. |
| 5,483,022 A | 1/1996 | Mar |
| 5,558,672 A | 9/1996 | Edwards et al. |
| 5,575,810 A | 11/1996 | Swanson et al. |
| 5,634,462 A | 6/1997 | Tyler et al. |
| 5,643,330 A | 7/1997 | Holsheimer et al. |
| 5,662,108 A | 9/1997 | Budd et al. |
| 5,683,422 A | 11/1997 | Rise |
| 5,702,429 A | 12/1997 | King |
| 5,702,438 A * | 12/1997 | Avitall ............... 607/122 |
| 5,713,922 A | 2/1998 | King |
| 5,713,923 A | 2/1998 | Ward et al. |
| 5,716,316 A | 2/1998 | Cartier et al. |
| 5,716,377 A | 2/1998 | Rise et al. |
| 5,733,322 A | 3/1998 | Starkebaum |
| 5,792,186 A | 8/1998 | Rise |
| 5,824,021 A | 10/1998 | Rise |
| 5,846,196 A * | 12/1998 | Siekmeyer et al. ......... 600/374 |
| 5,925,070 A | 7/1999 | King et al. |
| 5,954,665 A | 9/1999 | Ben-Haim |
| 6,014,588 A | 1/2000 | Fitz |
| 6,059,750 A | 5/2000 | Fogarty et al. |
| 6,161,047 A * | 12/2000 | King et al. ............... 607/62 |
| 6,205,361 B1 | 3/2001 | Kuzma et al. |
| 6,292,702 B1 | 9/2001 | King et al. |
| 6,319,241 B1 | 11/2001 | King et al. |
| 6,415,187 B1 | 7/2002 | Kuzma et al. |
| 6,442,435 B2 * | 8/2002 | King et al. ............... 607/117 |
| 6,522,932 B1 | 2/2003 | Kuzma et al. |
| 6,714,822 B2 * | 3/2004 | King et al. ............... 607/117 |
| 6,717,822 B1 | 3/2004 | King et al. |
| 6,795,737 B2 * | 9/2004 | Gielen et al. ............. 607/117 |
| 2001/0023367 A1 | 9/2001 | King et al. |
| 2001/0053885 A1 | 12/2001 | Gielen et al. |
| 2002/0151948 A1 | 10/2002 | King et al. |

FOREIGN PATENT DOCUMENTS

| | | |
|---|---|---|
| EP | 0499491 | 8/1992 |
| WO | WO 9304734 | 3/1993 |
| WO | WO 9407413 | 4/1994 |
| WO | WO 9634560 | 11/1996 |
| WO | WO 9639932 | 12/1996 |
| WO | WO 9732532 | 9/1997 |
| WO | WO 9955411 | 11/1999 |

OTHER PUBLICATIONS

Holsheimer and Wesselink, "Medical and Biological Engineering & Computing," vol. 35, pp. 493-497, 1997.

MR Assessment of The Normal Position of the Spinal Cord In The Spinal Cord, Holsheimer et al., Am. J. Neuroradiol., vol. 15, pp. 951-959, May 1994.

Notification of Transmittal and PCT Search Report for International Application No. PCT/US99/08734 mailed Dec. 28, 1999.

* cited by examiner

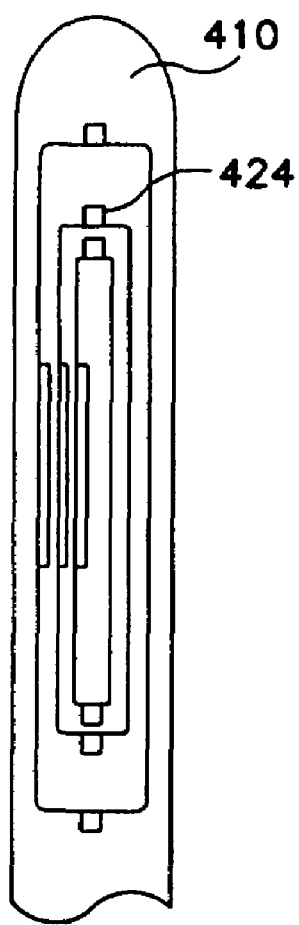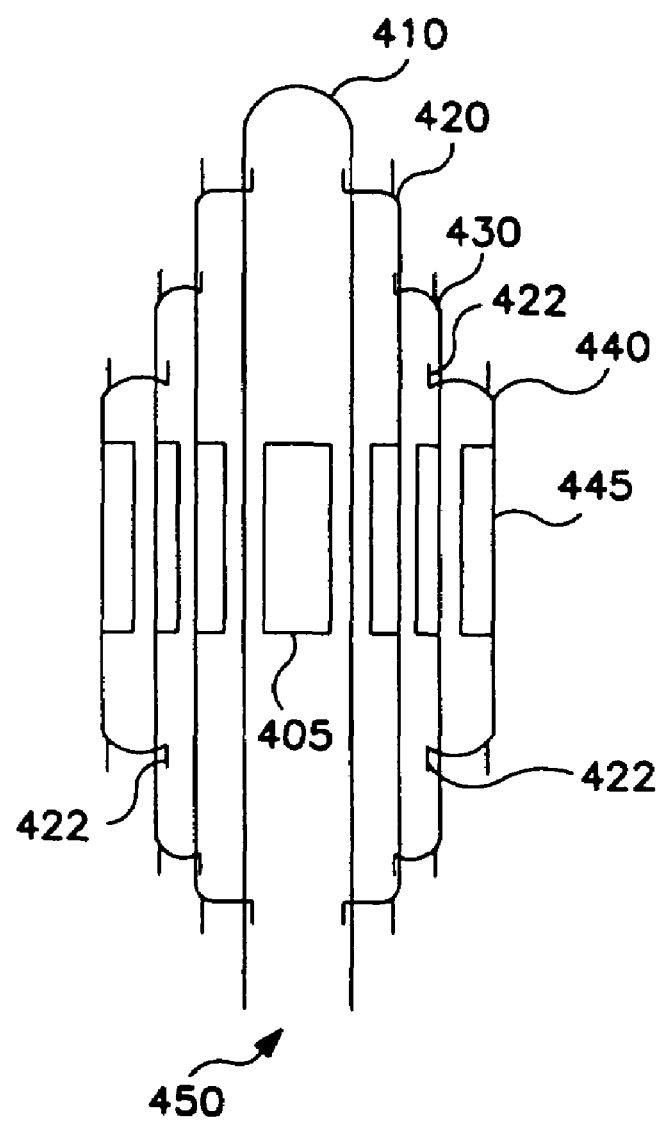
FIG. 9A
FIG. 9B

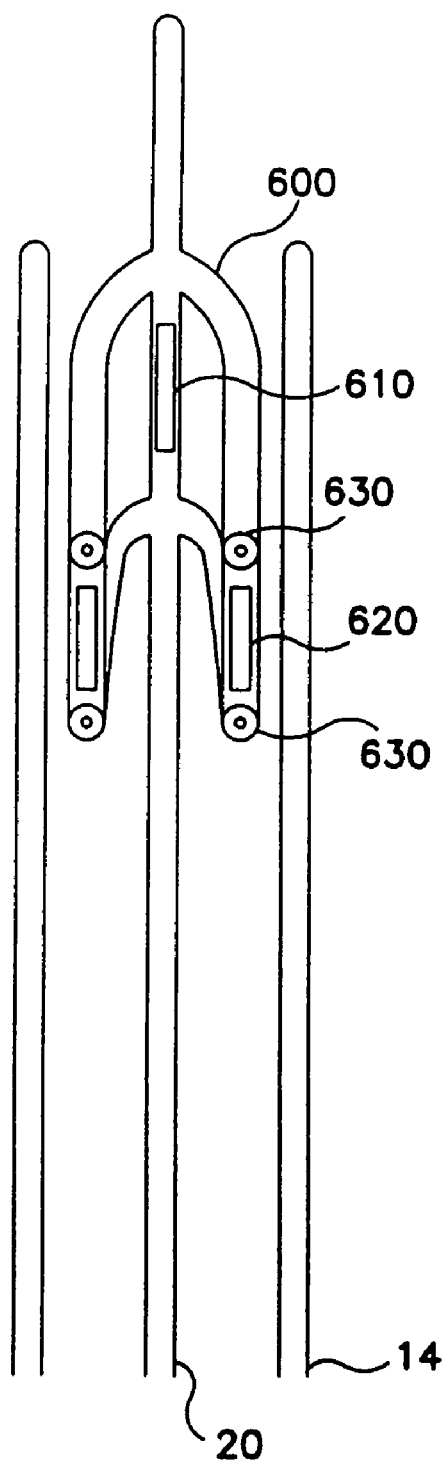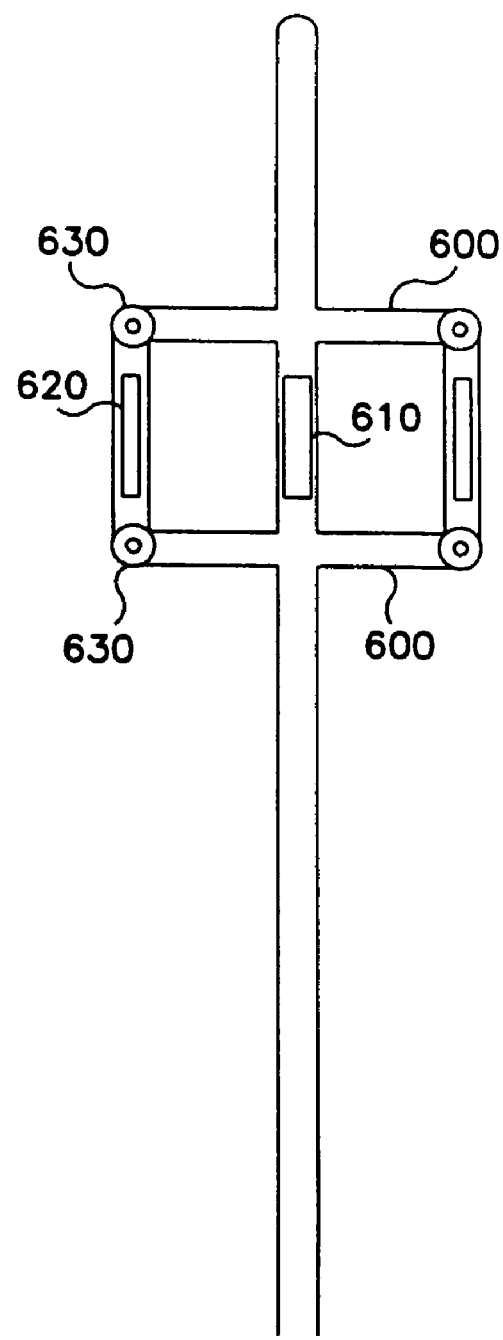
FIG. 11A
FIG. 11B

APPARATUS AND METHOD FOR EXPANDING A STIMULATION LEAD BODY IN SITU

RELATED APPLICATION

This is a continuation of 10/158,521, filed May 30, 2002, now U.S. Pat. No. 6,714,822 which is a divisional application of U.S. Ser. No. 09/862,104 filed May 21, 2001, now U.S. Pat. No. 6,442,435 which is a continuation of application Ser. No. 09/584,572 filed May 31, 2000, now U.S. Pat. No. 6,292,702, which is a divisional of U.S. Pat. No. 09/070,136 filed Apr. 30, 1998, now U.S. Pat. No. 6,161,047 for which priority is claimed.

BACKGROUND OF THE INVENTION

This invention relates to implantable leads for delivering therapy, in the form of electrical stimulation or drugs, to the human body. Specifically, this invention relates to implantable leads that may be expanded, retracted or adjusted after implantation in the human body. This invention also relates to mechanisms for accomplishing such expansion, retraction or adjustment of such leads in situ. Further, this invention relates to control systems for controlling such expansion, retraction or adjustment of such an implanted lead.

Recent efforts in the medical field have focused on the delivery of therapy in the form of electrical stimulation or drugs to precise locations within the human body. Therapy originates from an implanted source device, which may be an electrical pulse generator, in the case of electrical therapy, or a drug pump, in the case of drug therapy. Therapy is applied through one or more implanted leads that communicate with the source device and include one or more therapy delivery sites for delivering therapy to precise locations within the body. In drug therapy systems, delivery sites take the form of one or more catheters. In electrical therapy systems, they take the form of one or more electrodes wired to the source device. In Spinal Cord Simulation (SCS) techniques, for example, electrical stimulation is provided to precise locations near the human spinal cord through a lead that is usually deployed in the epidural space of the spinal cord. Such techniques have proven effective in treating or managing disease and acute and chronic pain conditions.

Percutaneous leads are small diameter leads that may be inserted into the human body usually by passing through a Tuohy (non-coring) needle which includes a central lumen through which the lead is guided. Percutaneous leads are advantageous because they may be inserted into the body with a minimum of trauma to surrounding tissue. On the other hand the types of lead structure, including the electrodes or drug-delivery catheters, that may be incorporated into percutaneous leads is limited because the lead diameter or cross-section must be small enough to permit the lead to pass through the Tuohy needle.

Recently, the use of "paddle" leads, like Model 3586 Resume® Lead or Model 3982 SymMix® Lead of Medtronic, Inc., which offer improved therapy control over percutaneous leads, have become popular among clinicians. Paddle leads include a generally two dimensional set of electrodes on one side for providing electrical therapy to excitable tissue of the body. Through selective programmed polarity (i.e., negative cathode, positive anode or off) of particular electrodes, electric current can be "steered" toward or away from particular to tissue within the spinal cord or other body areas. Such techniques are described by Holsheimer and Struijk, Stereotact Funct Neurosurg, vol. 56, 199: pp 234-249; Holsheimer and Wesselink, Neurosurgery, vol. 41, 1997: pp 654-660; and Holsheirner, Neurosurgery, vol. 40, 1997: pp 990-999; the subject matter of which is incorporated herein by reference. This feature permits adjustment of the recruitment areas after the lead has been positioned in 15 the body and therefore provides a level of adjustment for non-perfect lead placement. Such techniques are disclosed in U.S. Pat. Nos. 5,643,330, 5,058,584 and 5,417,719, the subject matter of which is incorporated herein by reference. Additionally, the value of a transverse tripole group of electrodes has been demonstrated for spinal cord stimulation, as described by Struijk and Holsheimer, Med & Biol Engng & Comput, July, 1996: pp 273-276; Holsheimer, Neurosurgery, vol. 40, 1997: pp 990-999; Holsheimer et al., Neurosurgery, vol. 20, 1998. This approach allows shielding of lateral nervous tissue with anodes, like the dorsal roots and steering of fields in the middle under a central cathode by use of two simultaneous electrical pulses of different amplitudes.

One disadvantage recognized in known paddle leads is that their installation, repositioning and removal necessitates laminectomies, which are major back surgeries involving removal of part of the vertebral bone. Laminectomies are required because paddle leads have a relatively large transverse extent compared to percutaneous leads. Thus, implantation, repositioning and removal require a rather large passage through the vertebral bone.

Another disadvantage with paddle leads is that optimal positioning is often difficult during implant. For example, the transverse tripole leads described above work optimally if the central cathode is positioned coincident with the physiological midline of the spinal cord.

Such placement is difficult since the doctor cannot see the spinal cord thru the dura during implant. Moreover, lead shifting may occur subsequent to implant, thereby affecting the efficacy of the therapy delivered from the lead.

Yet another disadvantage recognized with paddle leads is that the lead position may change merely with patient movement. For example, when a patient lies down, the spacing between an epidural lead and the spinal cord decreases to a large extent, so that it is often is necessary to lower the amplitude of the stimulation by half. It is reasonable to assume that steering effects of a tripole lead might also be affected if the CSF width changes dramatically, or if due to patient twisting or activity, the orientation between the lead and spinal cord changes.

While the prior art has attempted to provide deformable leads, which may provide improved insertion characteristics or enhanced stability once inside the body, they have not succeeded in providing a device which remedies the aforementioned problems. For example, U.S. Pat. No. 4,285,347 to Hess discloses an implantable electrode lead having a distal end portion with a laterally extending stabilizer, preferably in the form of curved loops. Similarly, and U.S. Pat. No. 4,519,403 to Dickhudt discloses an inflatable lead for enhanced contact of the electrode with the dura of the spinal cord. U.S. Pat. No. 5,121,754 to Mullett discloses a device to allow electrodes to move to more lateral positions after insertion, when a stiffening guidewire used during insertion is removed. In Mullett's device, only one electrode can be found at any particular longitudinal location, since only gentle curves of the lead were designed, and the curves are not adjustable after implant of the lead. Similar problems apply to the device disclosed by O'Neill in U.S. Pat. No. 4,154,247.

Patent Cooperation Treaty (PCT) Publication No. WO 93/04734 to Galley discloses a lead tip that has four spans that will bulge into four different directions when a confining outer catheter is drawn proximally back over the lead body. The publication describes one electrode on the middle of each span. In situ in the epidural space, these four electrodes will form a square or rectangular cross-sectional shape. Two of them might be pressed into the dura (at lateral positions) and the other two would be dorsal, against the vertebral bone. Only the electrodes nearest the spinal cord would be useful for programming. While this could give two electrodes at the same longitudinal position, their medial to lateral locations are difficult to control, and their ability to spread apart depends on the relative stresses in the spans and tissue-like adhesions that may be present. Other malecot-type lead tips have been proposed for positioning of electrodes in the heart (U.S. Pat. No. 4,699,147, Chilson and Smith, 1985; U.S. Pat. No. 5,010,894, Edhag, 1989) or anchoring of lead bodies (U.S. Pat. No. 4,419,819, Dickhudt and Paulson, 1982; U.S. Pat. No. 5,344,439, Otten, 1992) or positioning of ablation electrodes (Desai, U.S. Pat. Nos. 5,215,103, 5,397,339 and 5,365,926). While the aforementioned prior art devices provide various configurations for compact insertion or lead stabilization after implant, they do not offer the advantages and improved efficacy recognized with respect to paddle lead configurations.

It would therefore be desirable to provide a lead structure for stimulation of excitable tissue surfaces which combines the advantages offered by percutaneous leads with respect to minimized trauma during insertion, repositioning and removal with the advantages offered by paddle-type leads with respect to improved efficacy, ability to provide electrodes in places lateral to the axis of the lead and tailoring of treatment.

It would also be desirable to provide a lead structure which permits adjustment of the lead dimensions and therefore the delivery site location in situ for enhanced control of the therapy being applied to the excitable body tissues.

It would be further desirable to provide a paddle lead which is capable of automatically adjusting its width or delivery site spacing automatically in response to patient factors such as body position or activity or in response to a parameter such as muscle contraction or action topotentials, which may be characteristic of the stimulation or therapy being applied.

SUMMARY OF THE INVENTION

The invention combines the advantages of percutaneous leads with those of paddle leads. In a preferred embodiment, the invention provides a lead structure including a central core portion and at least one flexible, semi-flexible or semi-rigid transversely extending span which may be positioned in a compact position during insertion in which it is wound around or otherwise disposed in close proximity to the central core portion. Each span may also be deployed or shifted to a position in which it extends outward from the central core portion in a transverse direction. Each span has disposed on one surface a number of therapy delivery elements, in the form of electrodes or catheter ports, for delivering therapy in the respective form of electrical or drug therapy to the body. In the compact insertion position, the lead may be easily inserted within a catheter or Tuohy needle. Once the lead has been positioned at the appropriate place in the body, the span or spans may be deployed from the compact position to the extended position in which the therapy delivery elements are positioned in a fashion similar to a paddle lead. The flexibility of the spans also permits the lead to be retracted back to the compact position in the event that the lead must be removed from the body.

In a preferred embodiment, the invention provides a lead which includes a central core portion and at least one flexible paddle extending therefrom and which may be coiled around the core portion when the lead is to be compacted for insertion. As the lead is inserted through a catheter or Tuohy needle, the spans are kept in the compact position by lead rotation in a direction opposite their direction of winding around the central core. Also according to the invention, the spans are deployed by rotating the central core portion in the same direction in which the spans are coiled around the central core portion. Because of the flexibility of the spans, they are caused to move outward, away from the central core as the lead is uncoiled. In another embodiment of the invention, the spans can be formed of a resilient material in which resilient forces develop when the lead is configured in its compact position. The lead is maintained in its compacted form while inside of the insertion tool, i.e. Tuohy needle. The resilient forces cause the spans to extend outward once the lead exits the end of the insertion tool.

An outer concentric retainer tube may be provided in combination with the lead, the outer retainer tube acting to retain the lead in its compact position during insertion. The retainer tube may be provided with a pair of notches on its distal end to aid in the retraction of the lead after deployment. Specifically, the notches are disposed on the distal end of the retainer tube in such a manner that the spans will engage the notches when the central core portion is rotated and pulled toward a proximal end of the retainer tube. The notches retain the spans in position as the central core rotates, thus causing the spans to coil around the central core portion and assume a compact position.

The present invention also provides a lead which may be compacted in a different manner than described above. The lead is comprised of a series of therapy delivery elements which are attached to a thin backing sheet which permits the sheets to be disposed one on top of the other in the compact insertion position and then to expand to a generally planar orientation once the lead is inserted to the appropriate position in the body.

The following are exemplary advantages of adjustable leads constructed according to the preferred embodiments of the invention:

1. The spacing of the sites can be matched to important dimensions of the tissue affected, e.g., the width of the Cerebro-Spinal Fluid (CSF) between the dura and the spinal cord.

2. As the dimensions of the lead tip are changed, the locations of the sites relative to the tissue affected may be advantageously altered. For example, as a paddle's width is increased the paddle will move toward the spinal cord in the semicircular dorsal part of the epidural space.

3. In cases where the bones or fluid compartments have large widths (e.g., CSF depth at spinal level T7 or T8) or are too wide in a particular patient, the paddle width can be increased appropriately to ensure effective therapy.

4. Changes in paddle width and the accompanying medial and lateral movement of the sites can have a beneficial effect on the therapy. For example, the ability to stimulate only the medial dorsal columns versus the more lateral dorsal roots may provide enhanced therapeutic results.

5. As the patient ages, their pathological condition changes, their degree of fibrosis or scar tissue changes, or the effects of the therapy change, adjustments of the paddle dimension(s) might restore or maintain the benefit.

6. If the paddle's dimension(s) can be changed after implant, it may be possible to optimize the benefits and minimize undesirable side effects.

7. By changing the paddle's dimension(s), it may be possible to avoid surgery to replace or reposition the lead.

8. By changing the paddle's dimension(s), it may be possible to position the sites optimally relative to important physiological locations, e.g., the physiological midline of nervous tissue, or receptors responsive to the drugs being delivered.

9. It may be possible to minimize the use of energy by optimizing efficiency of therapy delivery through adjustment of paddle width.

10. There may be minimal insertion trauma and operating room time and resources needed if it is possible to place a lead with percutaneous techniques, and then expand it in situ.

11. Repositioning of a paddle lead can be done without laminectomy. Removal is also made quicker and less traumatic.

12. With closed loop feedback control of the paddle's dimension(s), optimal therapy can be maintained with less interference with the patient's lifestyle.

Another preferred embodiment allows automatic changes in at least one dimension of a paddle lead. Such a system would measure an effect of the stimulation, e.g., a compound action potential caused by stimulation/drugs, a muscle contraction, the direction of gravity, increased activity of the patient, relative motion of vertebral bones, or other effects. Measurement techniques for compound action potentials are disclosed in U.S. Pat. No. 5,702,429 the subject matter of which is incorporated herein by reference. Such a recorded signal should be altered if the lead paddle dimension that is controlled is changed. Then, after filtering, amplifying, integrating and comparing the recorded signal to a previous stored signal, the parts of the lead that control the dimension in question will be moved or activated, causing a change In said dimension, which will restore the effect measured to its original value. This constitutes closed loop feedback control, and can enable to patient to be less affected by changes in the therapy caused by his/her position, activity, etc. Of course there should be governors on the dimensional changes allowed, so that if the measured parameter is very greatly changed, neither the device nor the patient will undergo damage or trauma. The described embodiments show preferred techniques to expand a lead in directions transverse to the main axis of the lead body. The invention also contemplates devices for expanding the lead in a direction substantially parallel to the lead axis.

Other advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The advantages of the invention may be realized and attained by means of the instrumentalities and combinations particularly pointed out in the appended claims.

BRIEF DESCRIPTION OF THE DRAWINGS

The accompanying drawings which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout:

FIGS. 9A and 9B are side and front views, respectively, of another preferred embodiment of the present invention;

FIGS. 11A and 11B depict yet another preferred embodiment of the present invention;

DESCRIPTION OF THE PREFERRED EMBODIMENTS

Figure 1:
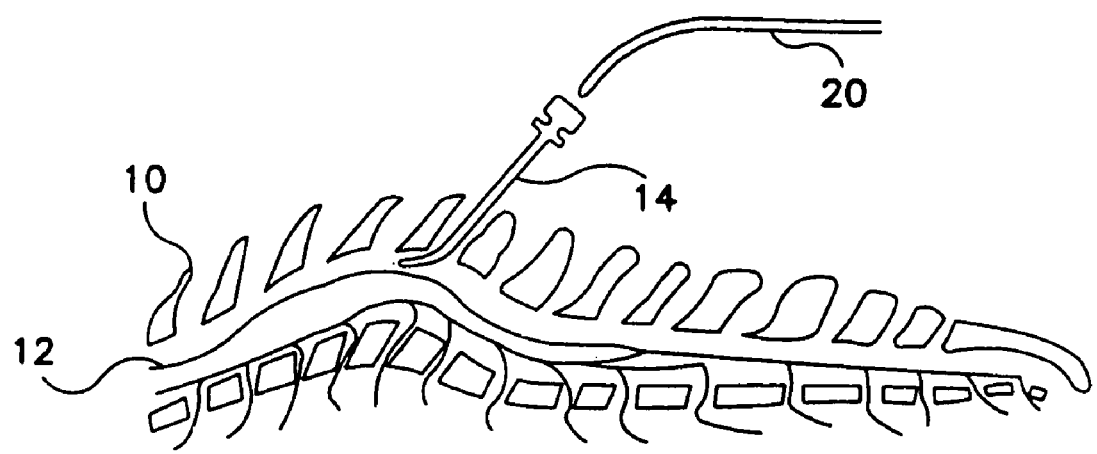
FIG. 1 is a plan view of a lead according to the present invention being inserted through a Tuohy needle near the dura of a human spine.

FIG. 1 illustrates a lead according to a preferred embodiment of the invention being utilized in an SCS implementation. In accordance with known techniques, a Tuohy needle 14 is positioned near the dura 12 of spine 10. Lead body 20 is inserted through the lumen of s Tuohy needle 14 and positioned near the dura 12. A proximal end (not shown) of lead body 20 is connected to a source device (not shown) which may be a pulse generator, in the case of electrical stimulation, or a drug pump in the case of drug therapy. Although the invention will be described herein with reference to SCS procedures and the embodiments described in relation to electrical therapy, it will be recognized that the invention finds utility in applications to other than SCS procedures, including other applications such as Peripheral Nervous System (PNS) Stimulation, Sacral Root Stimulation, Cortical Surface Stimulation or Intravecular Cerebral Stimulation. In addition, the invention finds applicability to SCS procedures where the lead is placed in the intrathecal (subdural) space. The invention also finds utility to drug therapy where electrical components are replaced with conduits and catheters for conducting is drug material to the therapy site. In this case, especially, the lead may be placed in the intrathecal space.

Figure 2A:
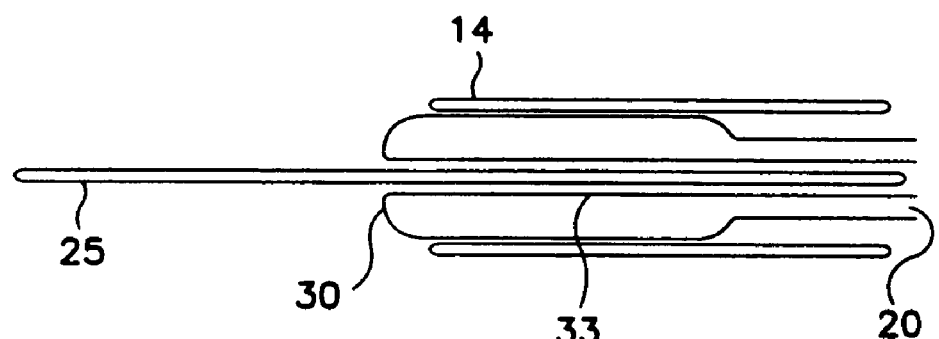
FIGS. 2A-2D are isometric views of a lead according to the present invention in a compact insertion position.
Figure 2B:
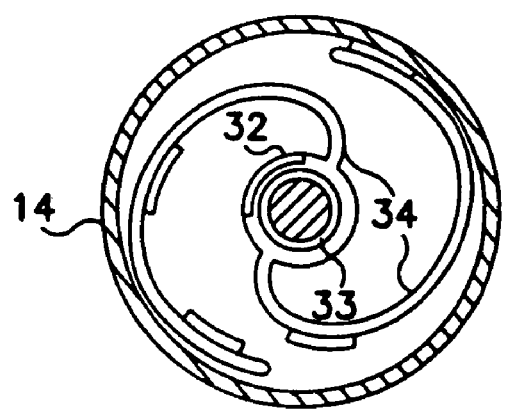

FIGS. 2A thru 2D illustrate a lead according to a preferred embodiment of the present invention. Lead 20 is provided with a distal tip 30 that may be compacted for insertion 20 and unfolded after it has been positioned appropriately within the body. Distal tip 30 includes a central portion 32 which has at least one span 34 depending therefrom. Span 34 is comprised of a flexible, insulative material, such as polyurethane or silicone rubber. The term "flexible" as used herein refers to both resilient and non-resilient materials. Central portion 32 may have a generally semi-circular cross-section as shown, or may be flat. A central passage 33 may run axially along the inside of lead 20. A centering stylet 25 is provided through central passage 33 and extends in a distal direction through central portion 32 for engaging a part of the body, such as adhesions in the epidural space, to stabilize lead tip 30 as it is deployed. Affixed to a surface of spans 34 and to the central portion 32 is a series of other therapy delivery elements in the form of electrodes 36A-E. In accordance with the invention, lead 20 may be configured into a compact insertion position shown in FIG. 2A. As shown in FIG. 2B, spans 34 are coiled around central portion 32 such that the lateral extent of lead tip 30 is no larger than the lumen of Tuohy needle 14.

Figure 2C:
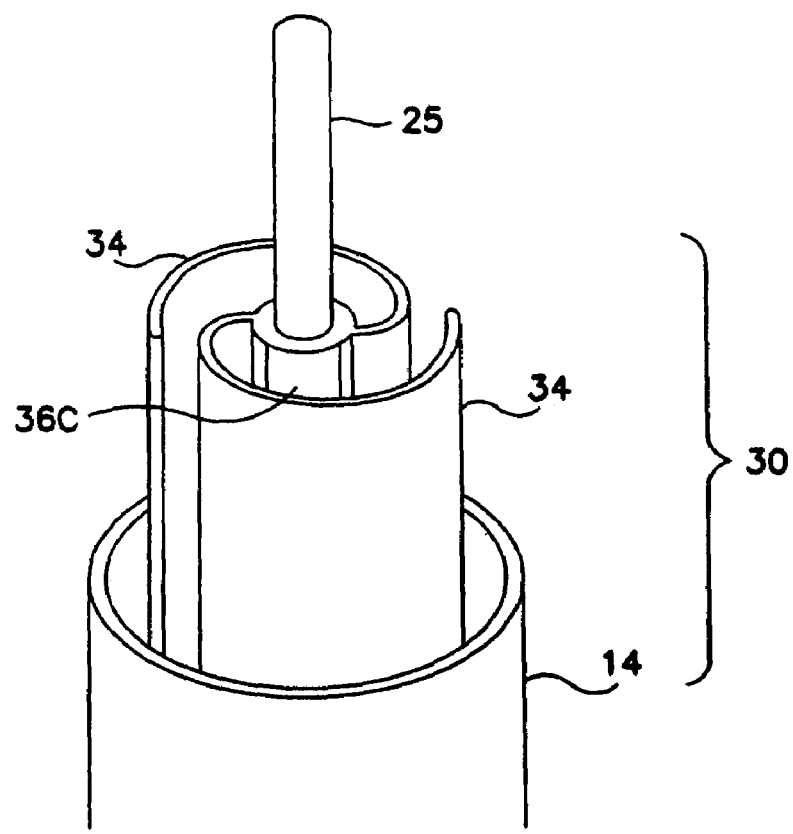
Figure 2D:
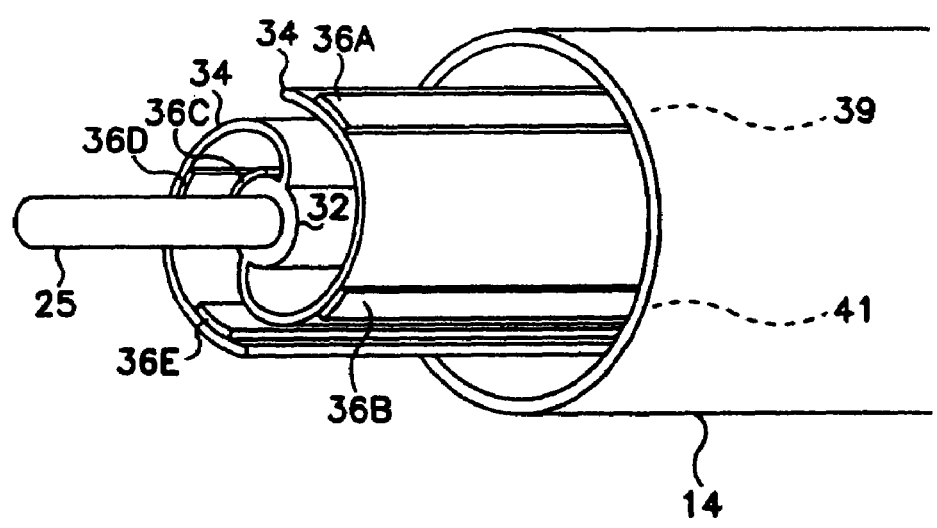
Figure 2E:
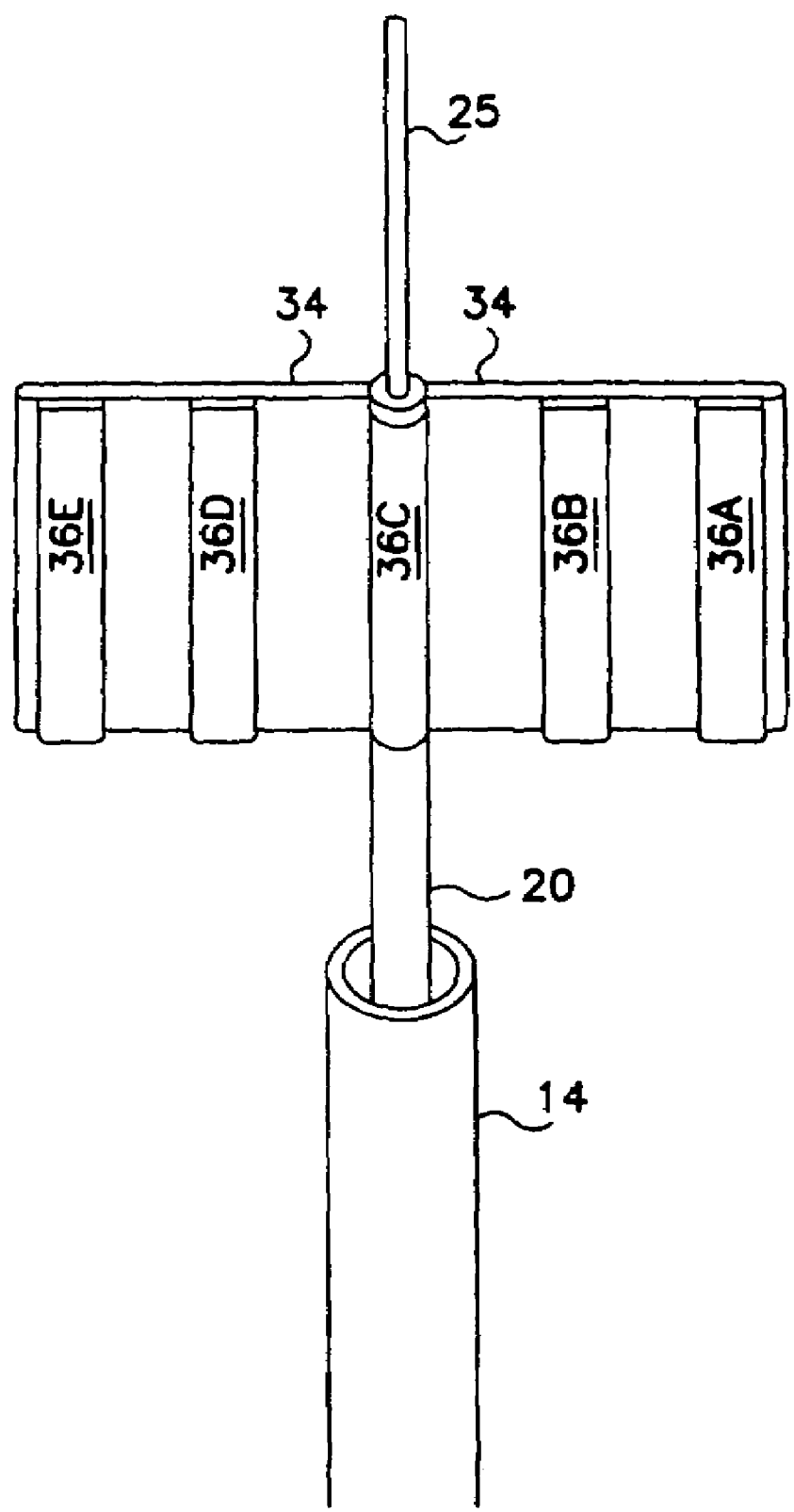
FIG. 2E is an isometric view of the lead of FIG. 2A in an expanded or deployed position.

Once in position within the epidural space, lead tip 30 may be deployed out of the Tuohy needle 14, as shown in FIG. 2C. FIG. 2D shows the view from the side opposite the side illustrated in FIG. 2C. In the embodiment described in which the spans are flaccid or to semirigid, deployment of lead tip 30 may be implemented by rotating the lead body 20 in a counterclockwise direction once lead tip 30 is beyond the end of the Tuohy needle in a desired position. As spans 34 encounter dura or dorsal bone of spinal canal, they can uncoil to assume a generally planar shape in which electrodes 36A-E are disposed on one side of the lead facing the dura, as shown in FIG. 2E. As shown in phantom in FIG. 2D, electrodes 36A-E communicate electrically with the source device (not shown) via conductor paths 39 and 41. Conductor paths 39 and 41 may be comprised of a flexible electrical conductor or thin wires which are embedded or molded within lead 20.

In the case of drug therapy, the electrodes 36A-E illustrated in FIGS. 2C-E would be replaced by ports which act as therapy delivery elements to convey drug to the body. Similarly, conductor paths 39 and 41 would be replaced by conduits formed in the interior of lead 20 for conveying drug from the source device. Stylet 25 may be left permanently in the epidural space or may be withdrawn from the lead 20 after the lead tip 30 is uncoiled. In the case of a drug delivery device, stylet 25 might remain as a catheter at some preferred distance.

Figure 3:
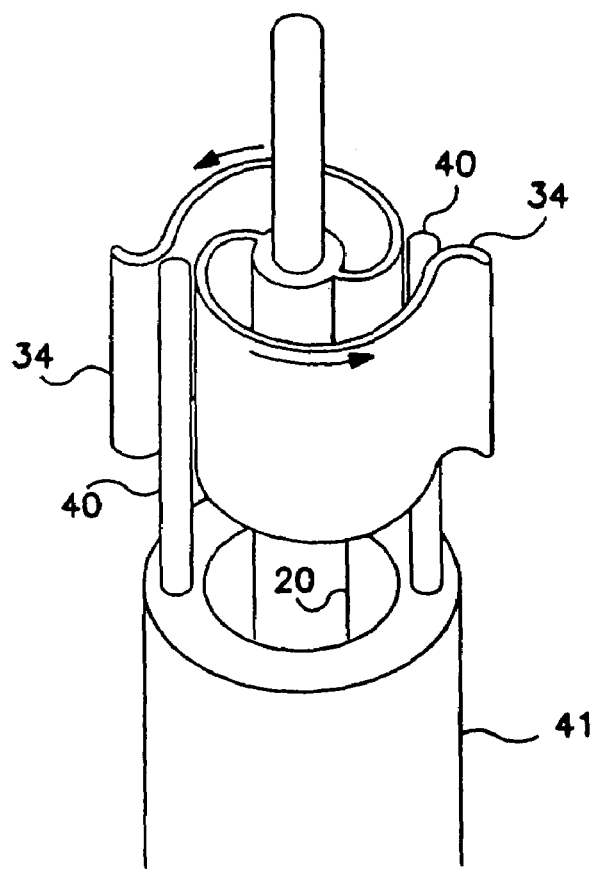
FIG. 3 is an isometric view of a lead according to another embodiment of the invention.

FIG. 3 illustrates another embodiment of the invention in which lead 20 is provided with a pair of guide pins 40 which are affixed to a more proximal removable sheath 41 that surrounds lead body 20. Alternatively, guide pins may be formed integrally on Tuohy needle (not shown). Guide pins 40 act to guide spans 34 outward as the lead body 20 is rotated in a counterclockwise and to guide spans 34 to coil around central portion as lead body 20 is rotated in a clockwise direction. Guide pins 40 may be comprised of a rigid, material and may be extended or retracted from sheath 41 or Tuohy needle 14. After spans 34 are deployed, sheath 41 may be removed.

Figure 4A:
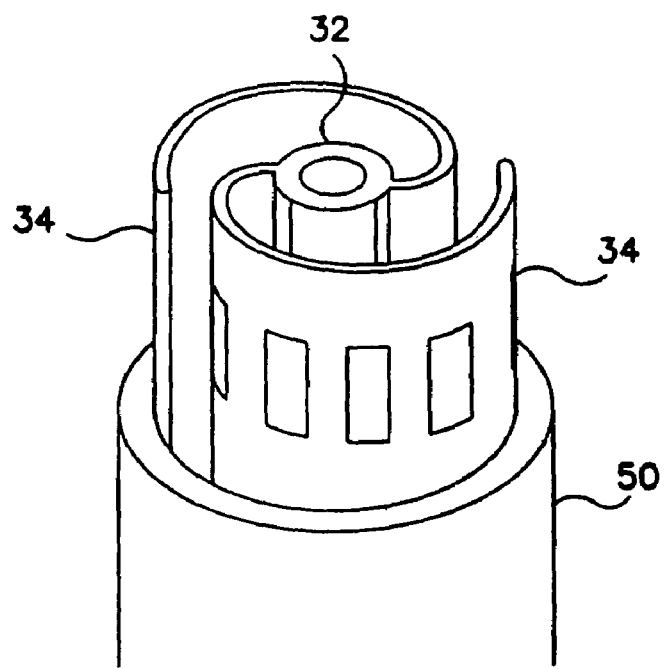
FIG. 4A is an isometric view of a lead and retainer tube according to yet another embodiment of the invention.

FIG. 4A illustrates another embodiment of the invention in which spans 34 are formed as resilient or elastic elements. The term "resilient" as used herein refers a tendency to return to an undeformed state once spans 34 are no longer compressed to lay beside central part 32. In accordance with this embodiment of the invention, a retainer tube 50 is provided to retain lead tip 30 in its compacted position until deployment is desired. Retainer tube 50 includes an inner passage which is sufficient to accommodate the diameter or lateral extent of lead body 20 and its compact shape-changing tip 30. The outer diameter of retainer tube 50 is small enough that retainer tube 50 may also be inserted through the lumen of Tuohy needle 14 (FIG. 1). Alternatively, tube 50 may replace the Tuohy needle. Spans 34 are formed in such a manner that they have a tendency to undertake a position in which they are extended from central portion 32. Thus, in the compact insertion position illustrated in FIG. 4A, resilient forces are present in spans 34 to urge them outward into their extended, uncoiled position. The resiliency of spans 34 may derive from the polymeric material used to construct spans 34 or from resilient elements like wires (not shown) which are incorporated into the interior or onto the exterior surface of spans 34.

Figure 4B:
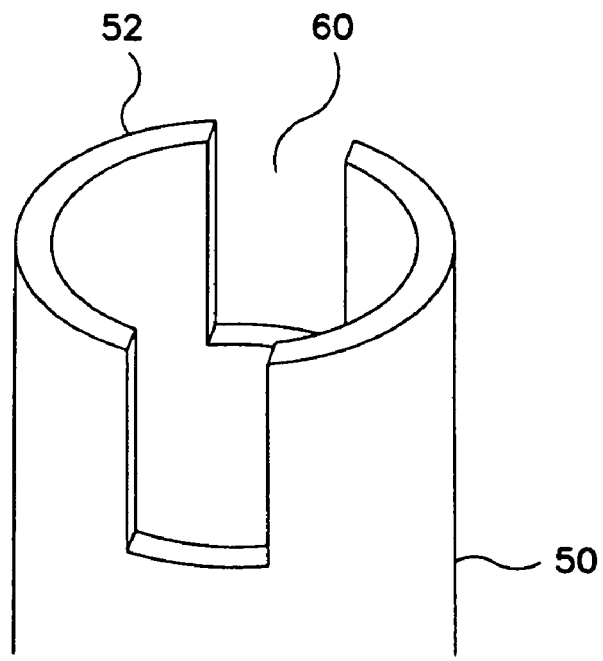
FIG. 4B is an isometric view of a lead retainer tube according to the present invention.
Figure 4C:
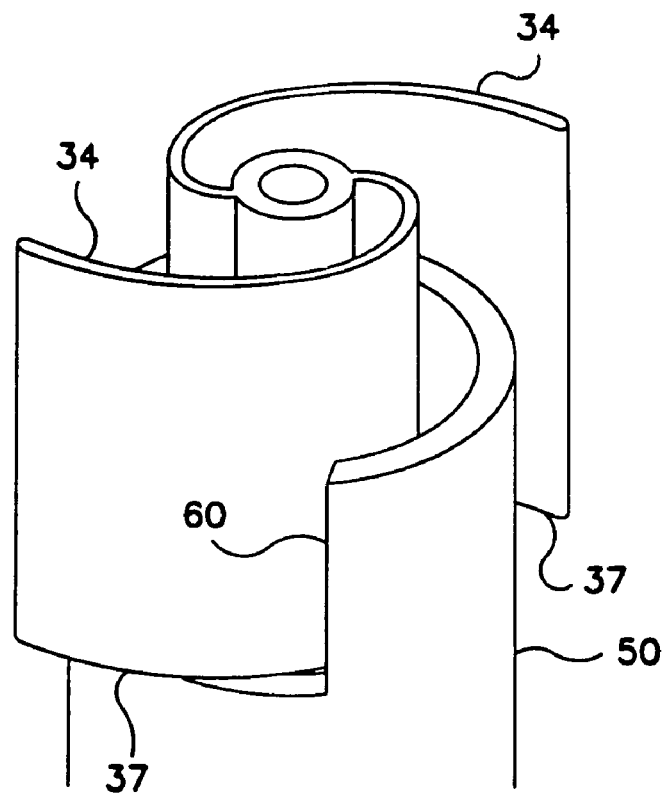
FIG. 4C is an isometric view of a lead and retainer tube according to the present invention.

Referring to FIGS. 4B and 4C, in accordance with yet another preferred embodiment of the invention, a notch 60 is provided in a distal end 52 of retainer tube 50 to facilitate retraction of a deployed lead. Preferably, one notch is provided for each span 34 provided on lead tip 30. In operation, retainer tube 50 is inserted around a proximal end (not shown) of lead body 20 and pushed towards lead tip 30 a sufficient distance until retainer tube 50 encounters lead tip 30. Lead body 20 is then pulled in a proximal direction and simultaneously rotated, in a direction which may be clockwise or counterclockwise, until lower edges 37 of spans 34 slide into notches 60. Under continued rotation of lead tip 30 and lead, notches 60 function to guide spans 34 into their coiled, compacted position. Once compacted, lead 20 may be retracted further into retainer tube 50. Compacted lead 20 and retainer tube 50 may then be repositioned to a higher or lower point along the spinal cord or may be removed from the body.

Figure 5A:
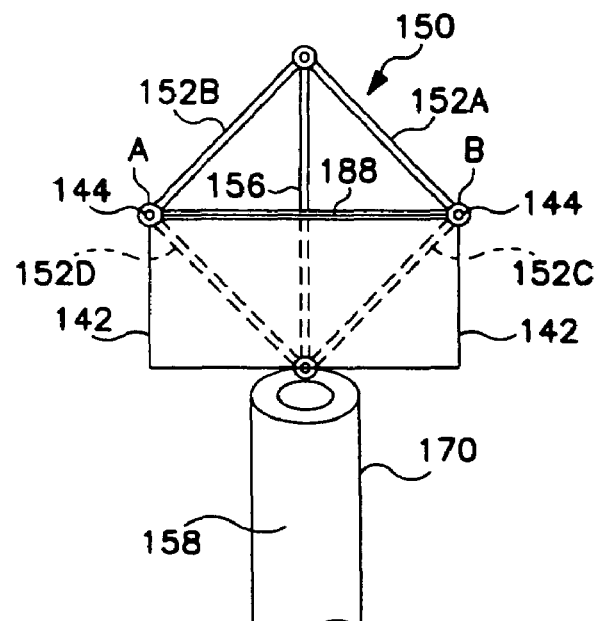
FIG. 5A is an isometric view of a lead and expansion mechanism according to another embodiment of the present invention.
Figure 5B:
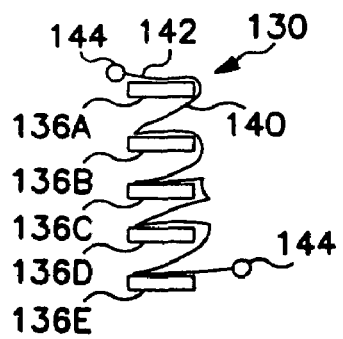
FIG. 5B is a top view of the lead of FIG. 5A in a compact position.

FIGS. 5A and 5B illustrate an expandable lead tip 130 according to another embodiment of the invention. Referring to FIG. 5B, lead tip 130 is comprised of a series of electrodes 136A-E which are fastened to a flexible insulative backing sheet or span 140. The central portion of lead tip 130 is comprised of middle electrode 136C. Span 140 may be constructed of polyurethane or DACRON-reinforced silicone rubber. Electrodes 136A-E are in electrical communication with source device (not shown) via a series of conductors 139 incorporated into or onto span 140. Electrodes 136A-E are embedded in span 140 or fastened by adhesive or other known means. Ends 142 of span 140 are provided with eyelets 144 for fastening to an expanding mechanism which will be described below. This aspect of the invention provides a lead tip 130 which may assume a compacted position, in which electrodes 136A-E are stacked one on top of the other such that the thickness of lead tip 130 may be reduced to a dimension that is slightly larger than the collective thicknesses of electrodes 136A-E.

Referring to FIG. 5A, lead tip 130 may be expanded with the use of an expansion mechanism 150 according to one aspect of the invention. Expansion mechanism 150 comprises a series of struts 152 which are pivotally linked to one another such that points A and B may be caused to move towards and away from one another in order to compact or expand lead tip 130, respectively. A first linkage 156 is pivotally connected to struts 152A and 152B. A second link 158 is pivotally connected to links 152C and 152D. First and second links 156 and 158 extend to a proximal end of lead body 20 where they can be individually actuated by a clinician. By moving first link 156 with respect to second link 158, points A and B are caused to move toward or away from one another, thereby contracting or expanding lead tip 130. By using rigid struts and linkages, sufficient farces can be applied so that a space may be created for the expanded size of lead tip 130. Introductory Sheath 170 may be removed after lead tip 30 is expanded. Or, as another embodiment, it might remain in the position shown, and a locking mechanism to keep links 156 & 158 at a constant position might be able to compress sheath 170 over the two links. A tether 188 sets a limit on the separation of points A and B, and guarantees that electrodes are evenly spaced when the length of tether 188 equals the length of span 140.

Figure 6A:
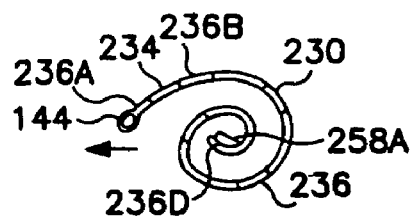
FIG. 6A is a cross section of a lead according to another embodiment of the invention.
Figure 6B:
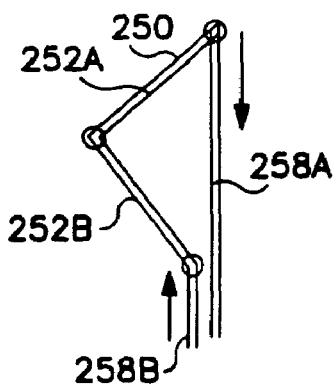
FIG. 6B is a front view of an expansion mechanism according to a preferred embodiment of the present invention.

FIGS. 6A and 6B illustrate another embodiment of the invention. FIG. 6A is a cross-section of a lead tip 230 according to a preferred embodiment of the invention which comprises a single span 234 incorporating a series of conductors 236A-F therein. FIG. 6B illustrates a plan view of a mechanism 250 suitable for deploying lead tip 230 or a stack of electrodes as shown in FIG. 5B. Mechanism 250 comprises a pair of links 252A and 252B pivotally connected to one another and each pivotally connected to a respective actuator link 258A and 258B. Through relative movement of actuator links 258A and 258B, point A is caused to move toward or away from link 258A, thereby causing contraction or expansion of lead tip 230 or 130. One eyelet 144 on span 234 is attached to point A, and the other eyelet may slide on link 258A. With this embodiment, since the lead tip is pulled in one direction, mechanism 250 in its initial, collapsed position should be positioned toward one side, for example, over the dorsal roots on one side of the spinal cord. In the expanded position, point A would advance to the opposite dorsal roots. Once again, a way to lock point A at a certain expanded position is to have an anchor along sheath 170 that compresses and holds sheath 170 against links 258A and 258B. Like mechanism 150, by using rigid struts and linkages, a space can be created for lead tip 230.

Figure 7:
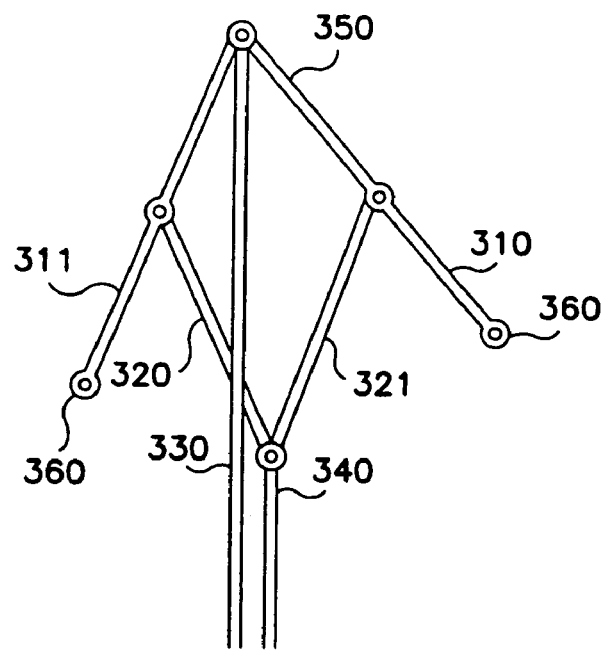
FIG. 7 is a front view of an expansion mechanism according to another preferred to embodiment of the present invention.

FIG. 7 illustrates an expansion mechanism according to another preferred embodiment of the invention. Lead tip 130 may be expanded with the use of mechanism 350, comprised of struts 311 and 310. Linkage 330 is pivotally connected to the end of these struts. Linkage 340 is pivotally connected to the center of these struts. As linkages 330 and 340 are moved relative to each other by a clinician, tips 360 will move together or apart. Eyelets 144 of lead tip 130 (FIG. 513) can be connected to tips 360.

Figure 8A:
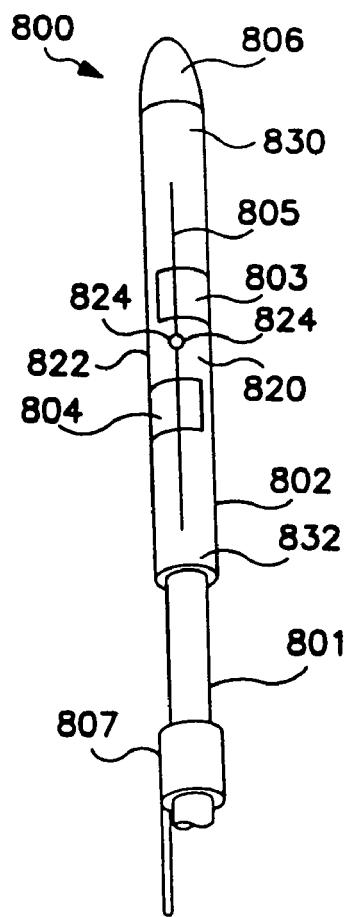
FIGS. 8A and 8B are front views of an expandable lead according to another preferred embodiment of the invention.
Figure 8C:
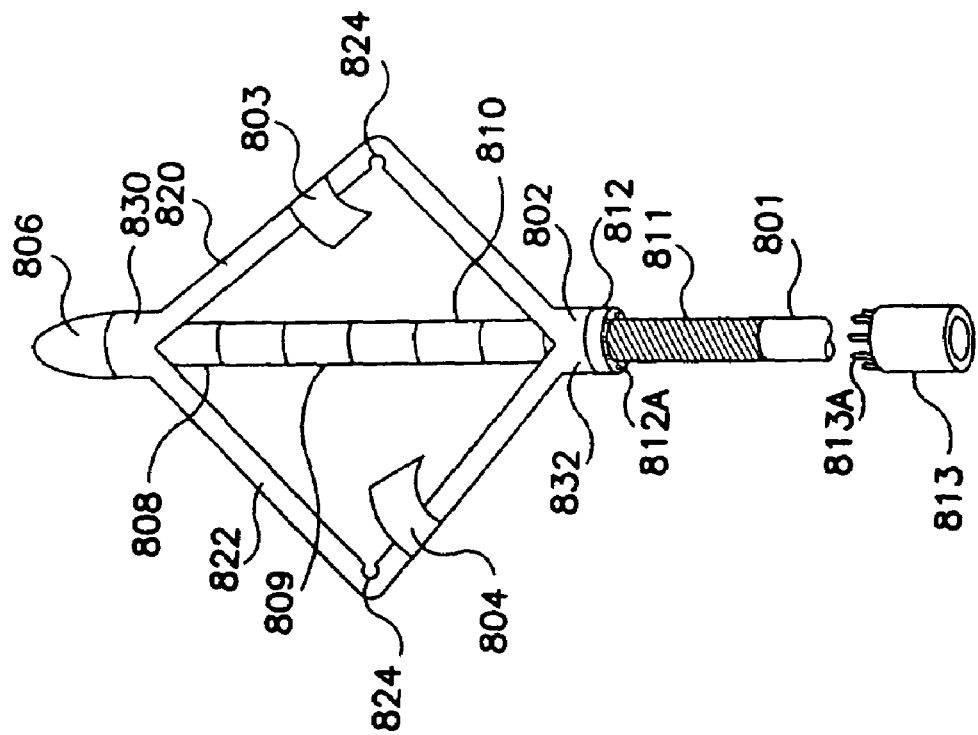
FIG. 8C is a front view of the expandable lead of FIGS. 8A and 8B with an alternative embodiment for the actuating mechanism.
Figure 8B:
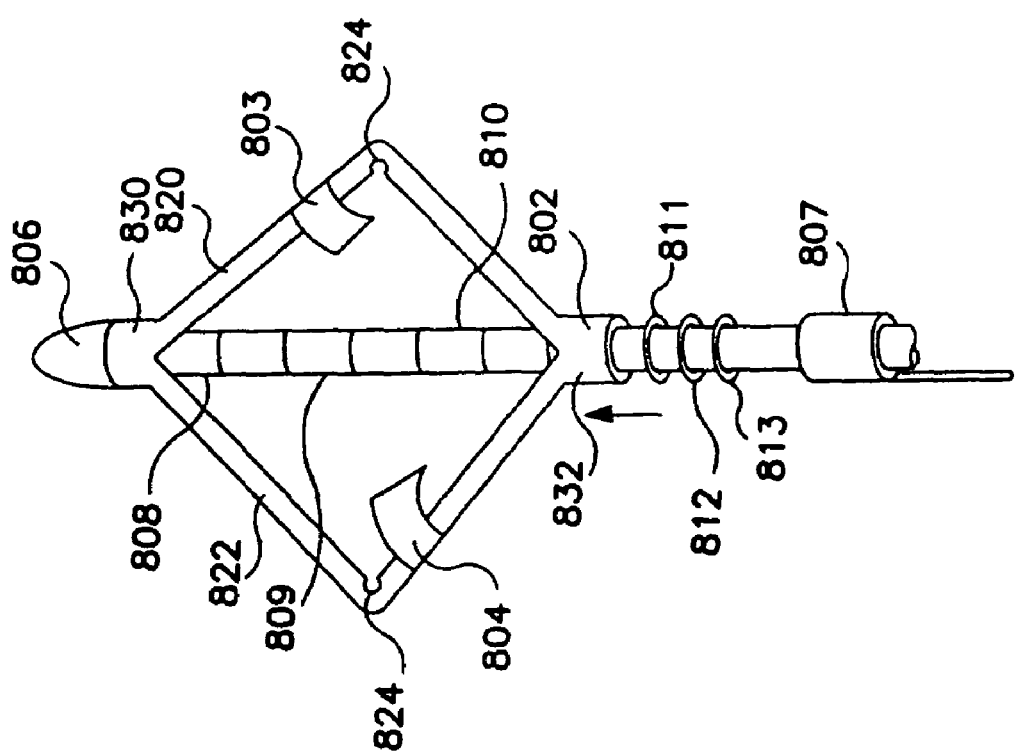

FIGS. 8A and 8B illustrate an expandable lead according to another preferred embodiment of the present invention. The lead comprises a flexible outer coaxial accessory tube 802 which is mounted over the distal end of lead body 801. A stop 806 is affixed to the distal end of lead body 801 to prevent movement of the upper end 830 of accessory tube 802 relative to lead body 801. The lower end 832 of accessory tube 802 is adapted to slide with respect to lead body 801. Accessory tube 802 includes a central slot 805 forming two flexible leaf portions 820 and 822. A recess 824 is provided in each leaf portion 820 to form a bending joint therein. The lower end 832 may be moved upward, thereby causing leaf portions 820 to bend and deploy outward from the lead body 801. To actuate the mechanism an actuator 807 is slid over the axial tube 801 by the clinician. While holding onto the axial tube 801, the clinician pushes the actuator 807 against the accessory tube which causes the slot 805 to separate and the lead to open as illustrated in FIG. 8B. A series of ratchet rings 811. 812 and 813 are formed in lead body 801 to prevent downward movement of lower end 832 of accessory tube 802 to thereby retain the leaf portions 820 in their outward, deployed position. These rachet rings will also allow and hold different amounts of lateral expansion to be chosen by the clinician. A rigid barrel electrode 803 is mounted on each leaf portion 820 of the accessory tube 802. In the expanded position of accessory tube 802, central electrodes 808, 809 and 810 are exposed. Central electrodes 808, 809 and 810 and barrel electrodes 803 communicate electrically with the source device (not shown) through electrical conductors (not shown) within the lead body.

FIG. 8C illustrates an expandable lead according to another preferred embodiment of the present invention. This embodiment is the same as that illustrated in FIGS. 8A and 8B except that a screw actuator is provided for precise adjustment of the outward deployment of leaf portions 820. The axial lead body 801 has a threaded portion 811 formed therein. A threaded drive nut 812 is mounted on the threaded portion of the lead body 811. The drive nut has multiple indented holes 812a to receive an actuation driver similar to 813. The drive nut is interlocked by pins (813a) on an actuation driver 813 and rotated by the driver. This screw apparatus allows finer adjustment of the expansion and also adjustment of the expansion after implantation of the lead device.

FIGS. 9A and 9B illustrate another embodiment of the invention. Mechanism 450 can have a central element 410 that may contain an electrode or catheter port 405. It may house progressively smaller mobile telescoping parts 420, 430, 440 that can be pushed outward toward one or more directions. Each mobile part is provided with a shoulder 422 to limit its outward movement and to recruit an adjacent mobile part. A tab 424 is provided to limit inward movements. For an expansion in one plane, element 410 may have inside it one or more mechanisms 150 (FIG. 5A), 250 (FIG. 6B) or 350 (FIG. 7).

Alternatively there might be single, curved linkage passing along lead 20 and attached to the final electrode or catheter port site 445. As this linkage is moved by a clinician, site 445 will move outward or inward, and intermediated sites will follow if the movement of each site relative to the next site is limited.

Figure 10A:
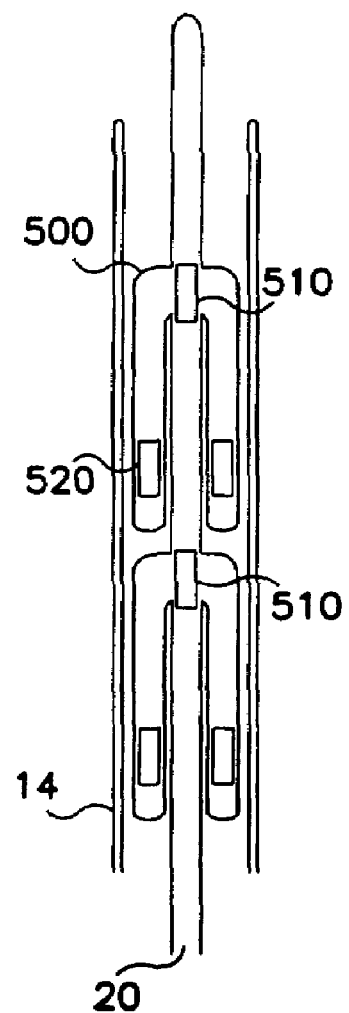
FIGS. 10A and 10B are front views of another preferred embodiment of the present invention.
Figure 10B:
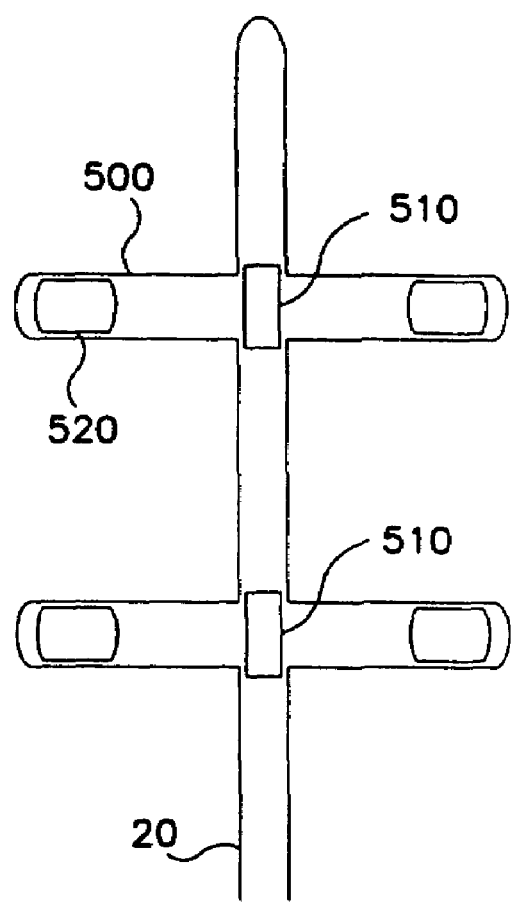

FIGS. 10A and 10B illustrate another embodiment of the invention. In FIG. 10A, the lead 20 is in a compacted position, with elastic and resilient transverse spans 500 bent to remain inside the lumen of Tuohy needle 14. Spans 500 are adapted to bend to a position substantially parallel to the axis of lead 20 in the compact position. Once the lead is pushed beyond the needle, spans 500 will move by their resiliency to their natural position, as shown in FIG. 10B. Those of ordinary skill will note that the grouping of central electrode or catheter port 510 and the two nearest side electrodes or ports 520 form a tripole/triport arrangement transverse to the longitudinal direction of the lead 20. The clinician may have to place and manipulate a mechanism like 150, 250 or 350 prior to placement of this lead to create a space. Alternatively, a metal material like NITINOL may be placed inside span 500 and treated so that its position after removal of the confinement of needle 14 will be perpendicular to the lead axis.

FIGS. 11A and 11B illustrate another embodiment of the invention. In FIG. 11A, the lead 20 is in a compacted position with elastic and resilient spans 600 bent to remain inside the lumen of Tuohy needle 14. There is a central electrode or catheter port 610. The lateral electrodes/ports 620 are on members that will remain parallel to the lead axis due to pivot points 630 and equal length spans 600 above and below.

In FIG. 11B, the lead tip is beyond the introducing needle. The spans 600 resume their normal, unstressed positions perpendicular to the lead body axis. Lateral electrodes/ports 620 are on either side of central electrode/port 610. Removal may be accomplished by pulling on the lead body with sufficient force to bend the spans 600 back along the lead body, or by pushing another catheter or needle over lead 20 It is recommended that there be a thin, inert and flexible film (not shown) over the space between spans to help removal by preventing tissue in growth. One embodiment of the invention is to lock linkages as shown in FIGS. 5-7 into a fixed orientation by using a compressive sleeve to squeeze the lead body 20 inward against the linkages. This sleeve may be an anchor to superficial (subcutaneous) tissue. To make a change, minor surgery can be done to cut down to this anchor, loosen or remove it, adjust the positions of the linkages, replace the anchor/compressive sleeve, and resutured the wound. Obviously, the clinician and patient need to believe that the benefits of such a procedure out weigh the discomfort and risks.

Figure 12A:
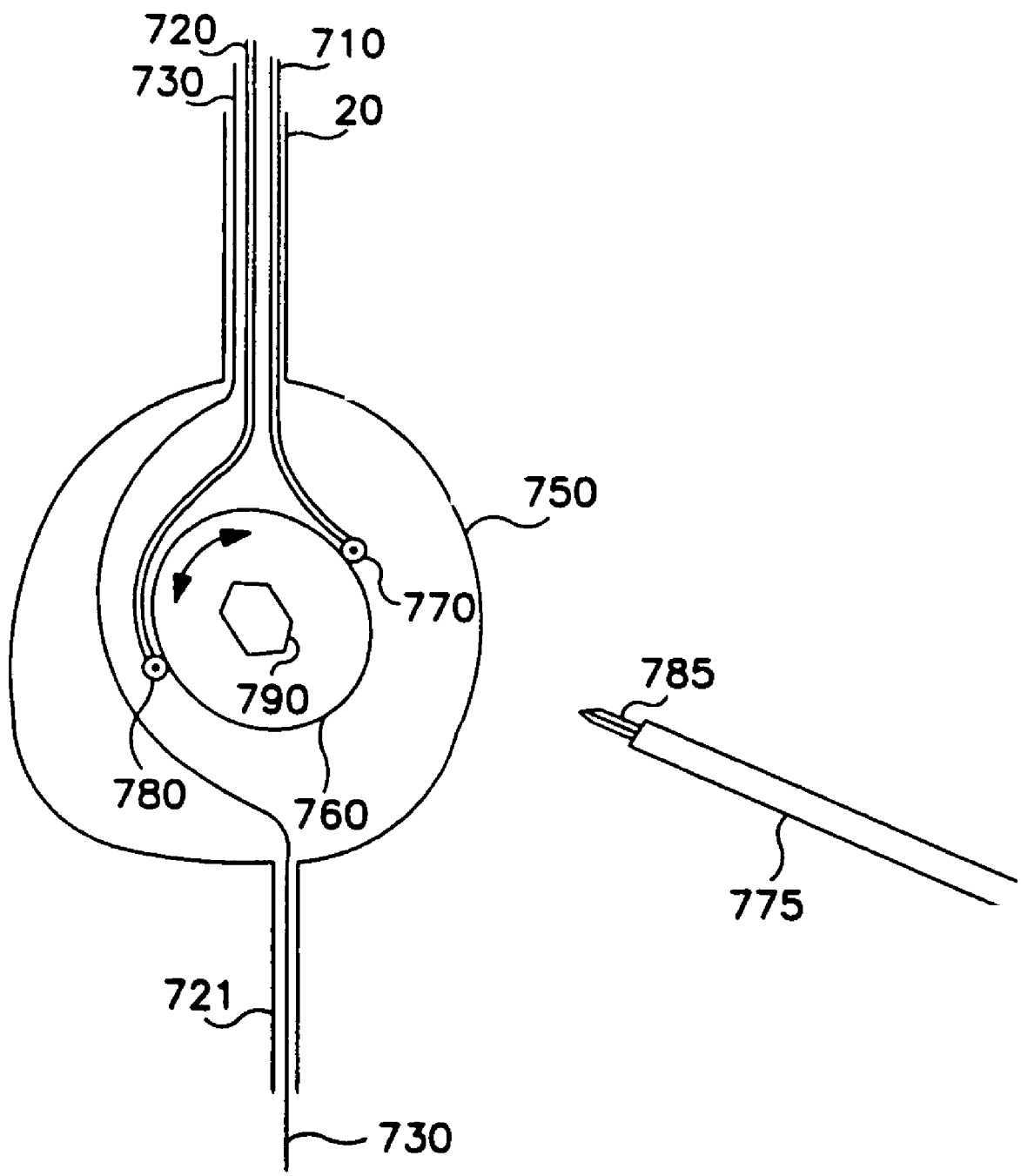
FIG. 12A is a front view of an adjustment mechanism according to a preferred embodiment of the invention.

FIGS. 12A through 12D illustrate mechanisms that may be used to operate the linkages illustrated and described with respect to FIGS. 5A, 6B, 7 and 9 in accordance with preferred embodiments of the invention. FIG. 12A illustrates an embodiment of the invention that allows chronic adjustment of the relative positions of two actuating members 710 and 720. A rigid needle 775 with a sharp hexagonal tip 785 is passed through the skin and engages a hexagonal receptacle (possibly via reduction gears) 790 that is capable of turning a circular component 760 inside of a container 750 beneath the patient skin. On end of this container 750 attaches to the lead body 20, which contains the two actuating members 710 and 720 and wires/catheters 730 that go to the distal tip of the lead 20. Another end of the container 750 connects to a lead 721 that conveys the wires/catheters 730 to a source device (not shown). Actuating members 710 and 720 are connected to the rotating component 760 are connected to the rotating component 760 by pivot points 770 and 780. As the needle 775 is rotated, the linkages 710 and 720 will move relative to each other. This device 750 should be -large enough to be palpated under the skin, and the rotating component 760 should be large enough so that limited rotation of approximately 60° causes sufficient movement of the linkages.

Figure 12B:
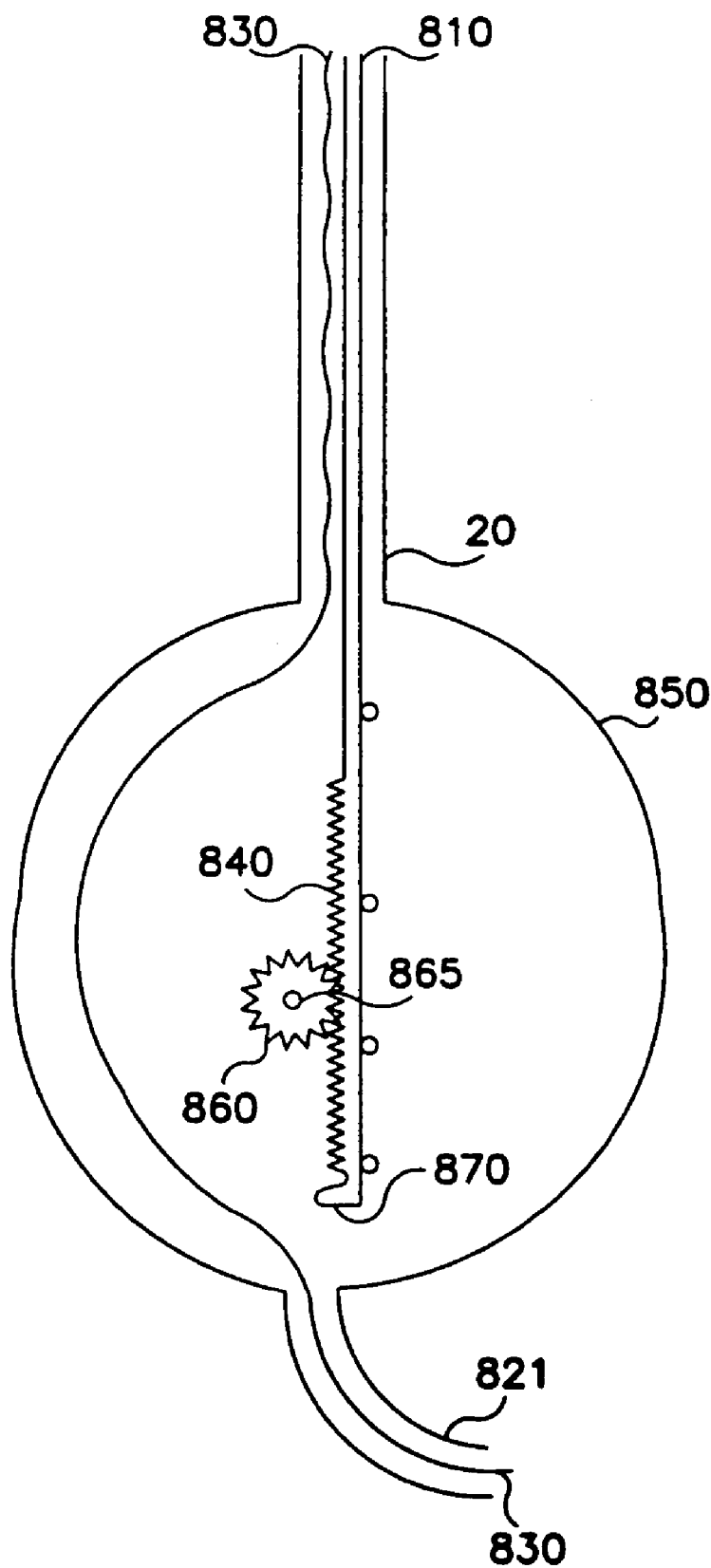
FIG. 12B is a front view of an adjustment mechanism according to another preferred embodiment of the invention.

FIG. 12B illustrates another preferred embodiment of a linkage actuating mechanism according to a preferred embodiment of the invention. This embodiment allows chronic adjustment of the position of one linkage 810 relative to the lead body 20 using a rack gear and pinion gear arrangement. This embodiment may be used with a two-actuating member configuration as described with respect to FIG. 12A, where one actuating member is fixed with respect to lead body 20. As in the embodiment described above with respect to FIG. 12A, a rigid needle (not shown) with a hex-head sharp tip is passed through the patient's skin and engages a hexagonal receptacle 865 that drives an internal gear 860 of subcutaneous container 850. As gear 860 turns possibly with the aid of reducing gears, it will, move the actuating member 810 back or forth, which has gear teeth 840 formed on its proximal end. A stop 870 prevents excessive movement of actuating member 810. A wire/catheter group 830 passes from lead 20 through the container to another lead 821 from the source device. Alternatively, the source device could be on the back side of the container 850. It will be recognized by those of ordinary skill that there could be a number of gears to inside container 850 to change the direction of movement of the actuating member 810, for example, to a rotary direction.

Figure 12C:
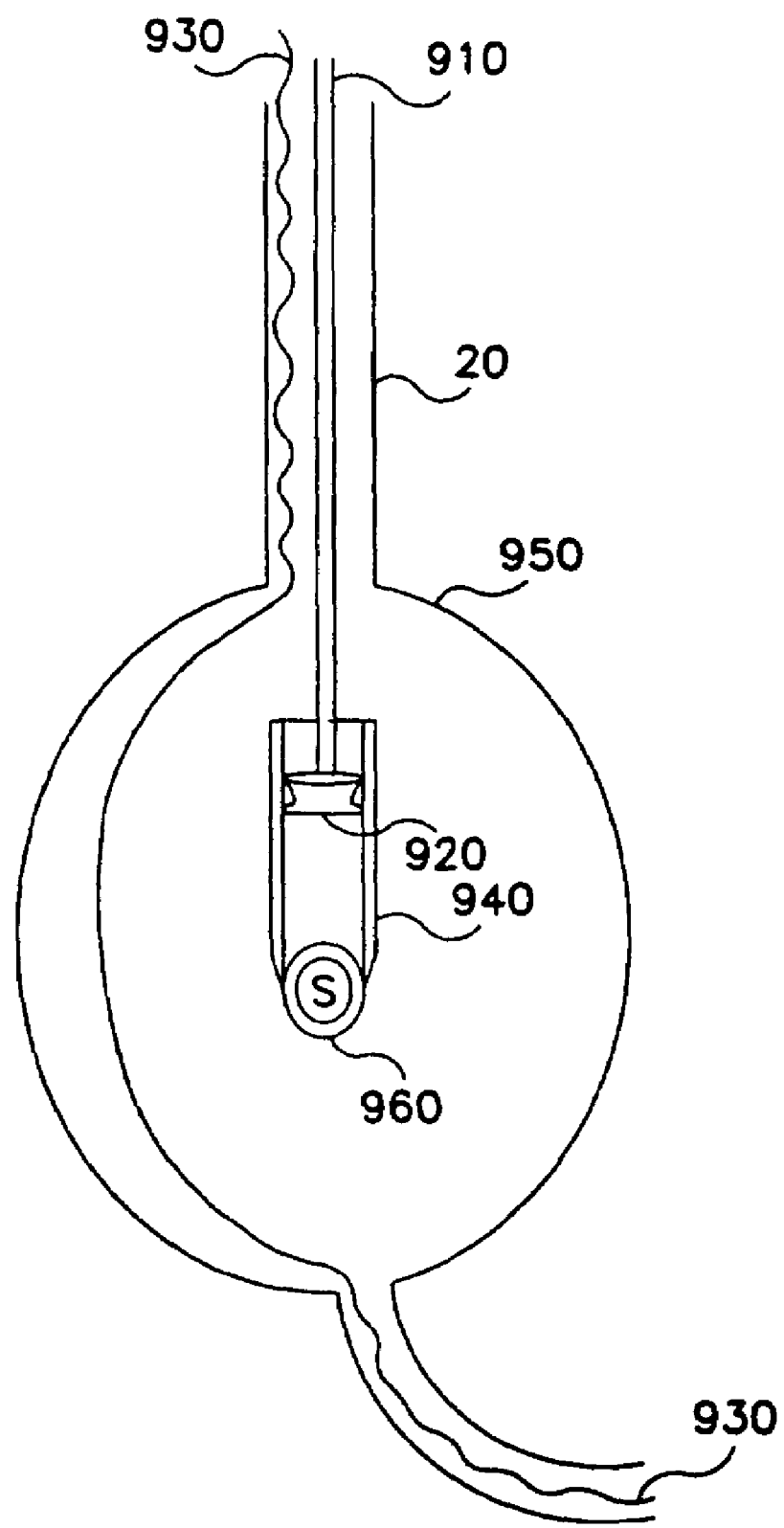
FIG. 12C is a front view of an adjustment mechanism according to yet another preferred embodiment of the invention.

FIG. 12C illustrates another preferred embodiment of a linkage actuating mechanism according to a preferred embodiment of the invention. This embodiment allows is chronic adjustment of the position of linkage 910 relative to the lead body 20. Again, this embodiment may be used with two linkage configurations where on linkage is fixed with respect to the lead body 20. This embodiment utilizes a hydraulic cylinder arrangement to actuate linkage 910. In this case a noncoring hypodermic syringe needle (not shown) is passed through the patient's skin and through a compressed rubber septum 960 provided on the side of container 950. Fluid may be added or withdrawn from beneath the septum, which is connected to a syringe 940. The moveable plug of this syringe 920 is connected to the moveable linkage 910. Again, the wires/catheters 930 from the proximal tip of lead 20 pass through container 950 and on to the source device. Alternatively, the source device could be on the back side of container 950, although, for drug delivery there would need to be another system on the front of container 950 for refilling the drug.

Figure 12D:
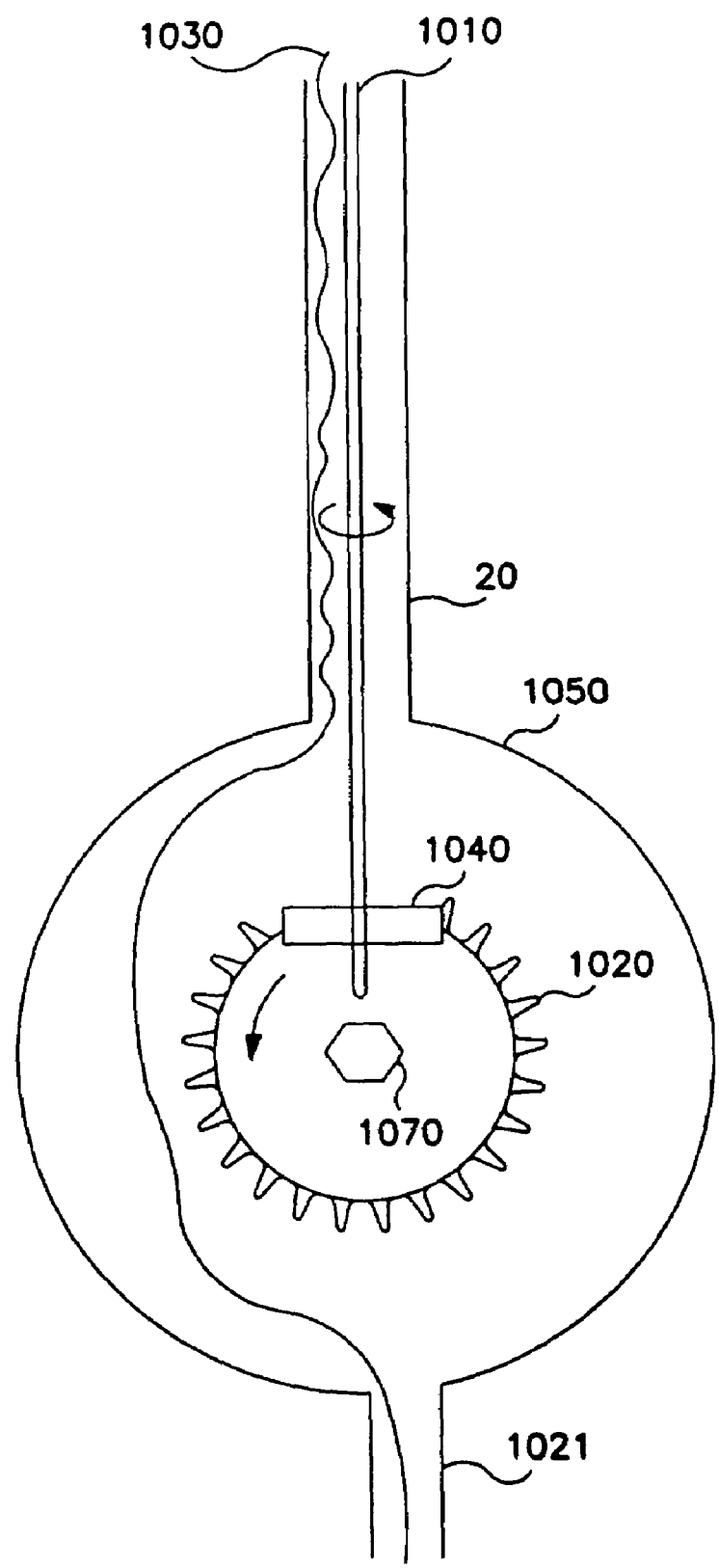
FIG. 12D is a front view of an adjustment mechanism according to still another preferred embodiment of the invention.

FIG. 12D illustrates an actuating mechanism according to a preferred embodiment of the present invention that allows chronic adjustment of the degree of rotation of linkage 1010 relative to lead body 20. A rigid needle with a hex-head sharp tip can be inserted into a hexagonal receptacle 1070 in container 1050. Rotation of this needle device rotates gear 1020 which causes rotation of gear 1040 attached to linkage 1010. There may be restrictions on the movement of gear 1020 to prevent excessive rotation.

The embodiments shown in FIGS. 12A-D demonstrate devices to actuate linkages that pass to the distal tip of the lead and cause changes in one or more dimensions of the lead paddle. As described, these involve transmission of force or energy through the skin by means to of a needle that passes through the skin. The same effects can be achieved by having a small motor implanted into the container parts shown, or into the power source itself (not shown) which runs on an electrical battery or transmitted and received radio frequency signal, such as the motor provided in the totally implantable, programmable drug device called SynchroMed®, manufactured by Medtronic, Inc. of Minneapolis, Minn. Smaller motors may be acceptable, especially if a sequence of gears may be used to provide mechanical advantage. If such motors are used, there should be a mechanical circuit breaker to prevent excess motion of the linkages.

Very similar techniques would allow expansion of a lead in a direction parallel to the lead body. For example, telescoping elements with electrodes could move parallel to the axis of the lead body (parallel to the spinal cord), similar to the way a car antenna can be extended and retracted. By attaching electrodes and catheter ports to the axial linkages of FIGS. 5 through 8, or attaching eyelets 144 of compacted groups of electrodes/ports such as items 130 or 230, it is possible to extend or compact said groups of electrodes in an axial direction. This is a valuable feature if one wishes to match the axial spacing of electrodes/ports to important dimensions of the structure to be stimulated/affected. For example, Holsheimer (Neurosurgery, vol. 40, 1997: pp 990-999) has shown that there may be preferred longitudinal spacing of electrodes based upon the recruitment factors in spinal cord tissue, and also critically dependent upon the width of the CSF (cerebrospinal fluid) layer between the spinal cord dorsal surface and the dura mater. Therefore, we wish to include the ability to increase or decrease the longitudinal spacing between electrodes/ports by these inventions, and to be able to make a change in said spacing after initial implant of a complete therapeutic system.

Those skilled in the art will recognize that the preferred embodiments may be altered or amended without departing from the true spirit and scope of the invention, as defined in the accompanying claims.

What is claimed is:

1. An implantable medical device for providing therapy to a body comprising:
   an elongate central portion having a longitudinal center of axis;
   at least one extendable member having a tip, the extendable member depending from the central portion and being adapted to assume a range of positions, including a contracted position, in which the tip is disposed in close proximity to the central portion, and an expanded position, in which the tip is disposed at a location distal from the central portion;
   at least one therapy element disposed on the extendable member for delivering therapy to the body;
   a linkage assembly for position adjustment of the extendable member in situ, the linkage assembly comprising a first pair of struts that are directly and pivotally linked to one another at a first point and a second pair of struts that are directly and pivotally linked to one another at a second point, the first point and the second point adapted to move towards each other to contract the extendable member, and away from one another to expand the extendable member;
   wherein the extendable member comprises a span having a first end and a second end that are fastened to the linkage assembly at the first point and the second point respectively, the span adapted to contract between the first point and the second point when the first point and second point are moved towards each other, and expand between the first point and the second point when the first point and the second point are moved away from each other, the span forming a paddle surface, the paddle surface having a longitudinal center of axis parallel to the longitudinal center of axis of the elongate central portion when the paddle surface is in the expanded position.

2. The implantable medical device of claim 1, wherein the linkage assembly comprises a first link and a second link, the first pair of struts comprising a first strut and a second strut, the second pair of struts comprising a third strut and a fourth strut, the first link pivotally connected to the first strut and the second strut, the second link pivotally connected to the third strut and the fourth strut, the first link moveable with respect to the second link to cause the first point and the second point to move toward or away from one another.

3. The implantable medical device of claim 2, further comprising a sheath that surrounds the span when the extendable member is in the contracted position.

4. The implantable medical device of claim 3, wherein the sheath is removeable after the extendable member has been expanded to the expanded position.

5. The implantable medical device of claim 1, further comprising a sheath that surrounds the span when the extendable member is in the contracted position.

6. The implantable medical device of claim 5, wherein the sheath is removable after the extendable member has been expanded to the expanded position.

7. The implantable medical device of claim 5, further comprising a locking mechanism to keep the extendable member at a constant position.

8. The implantable medical device of claim 1, further comprising a locking mechanism to keep the first link and the second link at a constant position.

9. The implantable medical device of claim 8, wherein the locking mechanism comprises a sheath compressed over the first link and the second link.

10. The implantable medical device of claim 1, further comprising a tether to limit the separation of the first point and the second point.

11. The implantable medical device of claim 1, wherein the span folds between the first point and the second point when the extendable member is in the contracted position, and unfolds between the first point and the second point when the extendable member is in the expanded position.

12. The implantable medical device of claim 1, further comprising a mechanism for adjusting the relative positions of the first point and the second point.

* * * * *